(12) United States Patent
Worth

(10) Patent No.: US 10,557,838 B2
(45) Date of Patent: Feb. 11, 2020

(54) PORTABLE GAS DETECTING AND MONITORING APPARATUS

(71) Applicant: Acrulog Pty. Ltd., Clontarf Qld (AU)

(72) Inventor: Brian Worth, Woody Point (AU)

(73) Assignee: Acrulog Pty. Ltd., Clontarf Qld (AU)

( * ) Notice: Subject to any disclaimer, the term of this patent is extended or adjusted under 35 U.S.C. 154(b) by 185 days.

(21) Appl. No.: 15/430,034

(22) Filed: Feb. 10, 2017

(65) Prior Publication Data

US 2017/0234845 A1 Aug. 17, 2017

(51) Int. Cl.
*G01N 33/00* (2006.01)

(52) U.S. Cl.
CPC ..... *G01N 33/0032* (2013.01); *G01N 33/0006* (2013.01); *G01N 33/007* (2013.01); *G01N 33/0009* (2013.01)

(58) Field of Classification Search
CPC .............. G01N 33/0006; G01N 33/00; G01N 33/0009; G01N 33/0032; G01N 33/007
See application file for complete search history.

(56) References Cited

U.S. PATENT DOCUMENTS

| | | | |
|---|---|---|---|
| 6,198,400 B1 * | 3/2001 | Church | G01N 33/0006 340/632 |
| 8,358,105 B2 * | 1/2013 | Barten | G01N 33/0009 320/108 |
| 2004/0145485 A1 * | 7/2004 | Tice | G08B 21/16 340/632 |
| 2013/0296723 A1 * | 11/2013 | Cho | A61B 5/02108 600/501 |
| 2014/0260543 A1 * | 9/2014 | Zielinski | G01N 19/10 73/29.02 |
| 2014/0260571 A1 * | 9/2014 | Stevens | G01D 7/005 73/73 |
| 2017/0154509 A1 * | 6/2017 | Prabhakar | G08B 17/06 |

\* cited by examiner

*Primary Examiner* — Randy W Gibson
*Assistant Examiner* — Gedeon M Kidanu
(74) *Attorney, Agent, or Firm* — Michael W. Goltry; Robert A. Parsons; Parson & Goltry, PLLC

(57) ABSTRACT

A portable gas detecting and monitoring apparatus includes a case having a continuous sidewall including a first end closed a first end cap, and a second end closed by a second end cap connected sealably and removably to the continuous sidewall. The continuous sidewall is triangular between the closed end and the open having three sides and three corners, two of the three sides being straight and equal in length, one of the three sides being rounded, and each of the three corners being rounded. A gas detection and monitoring unit mounted in the case includes gas, pressure, and temperature and humidity sensors in communication with an ambient atmosphere outside the case, a data processor operatively connected to the sensors, data storage, an information display viewable through the case, and a calibration unit for calibrating the gas sensor to a predetermined gas concentration measured by the gas sensor.

12 Claims, 2 Drawing Sheets

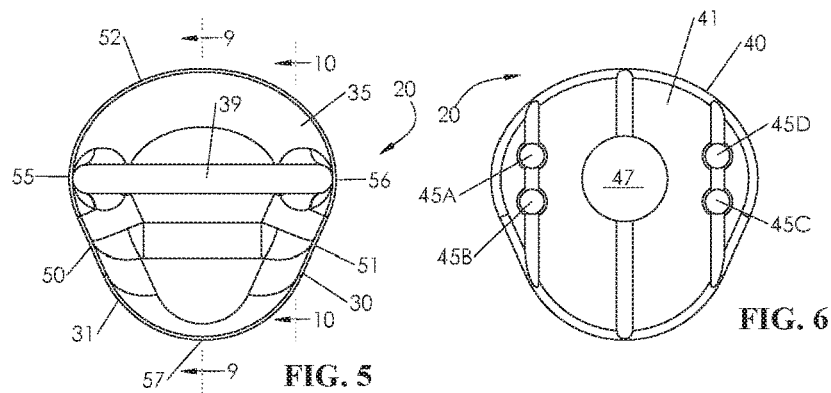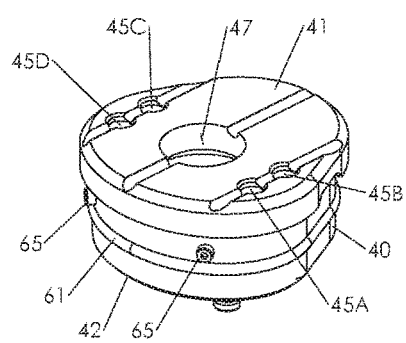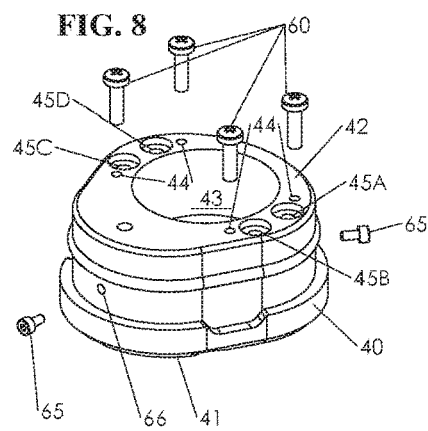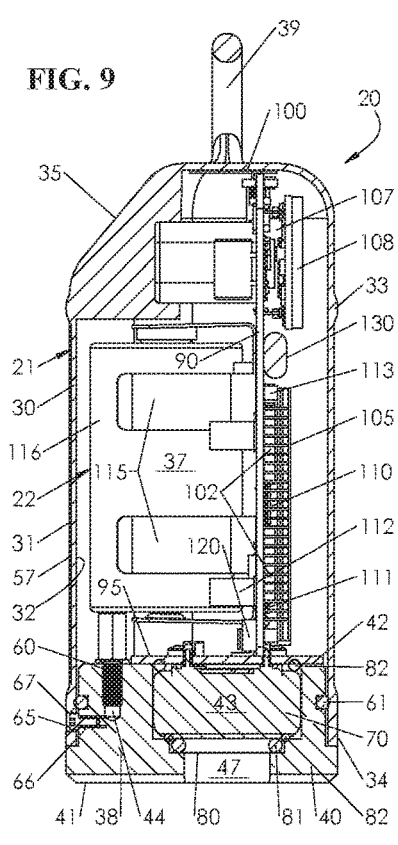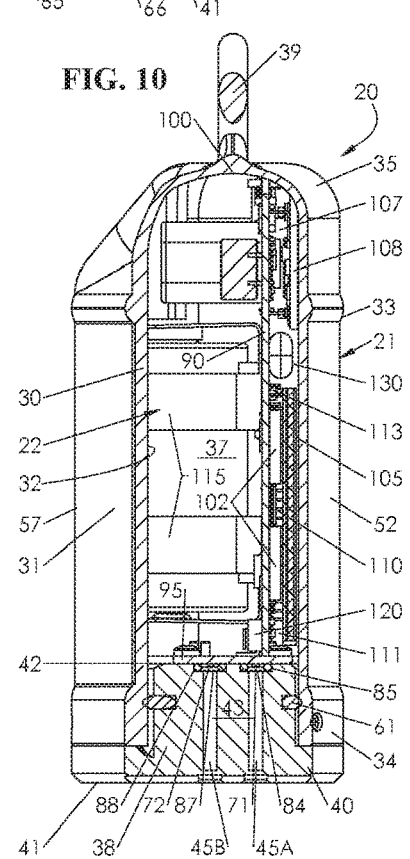

PORTABLE GAS DETECTING AND MONITORING APPARATUS

CROSS REFERENCE TO RELATED APPLICATION

This application claims the benefit of Australian Provisional Patent Application No. 2016900481, filed Feb. 12, 2016, the entire contents of which are incorporated herein by reference.

FIELD OF THE INVENTION

The present invention relates to apparatus and methods for detecting and monitoring gases in chosen environments, such as wastewater infrastructures and other hostile environments.

BACKGROUND OF THE INVENTION

Gas detectors for detecting and/or monitoring harmful and/or offensive gases are widely used in industry, such as in industrial plants, refineries, pharmaceutical manufacturing facilities, fumigation facilities, paper pulp mills, aircraft and ship-building facilities, hazmat operations, waste-water treatment facilities, and other hostile environments. Prior art gas detectors are inherently restricted in their capabilities and effective life in harsh or hostile environments due to the poor conditions and/or levels of corrosive substances and/or humidity. Moreover, sensor leakages and data loss due to excessive humidity uptake commonly occur in prior art gas sensors designed for use in hostile, humid environments. Given these and other deficiencies, the need for continued improvement in the art is evident.

SUMMARY OF THE INVENTION

A portable gas detecting and monitoring apparatus includes a gas detection and monitoring unit mounted in a case. The case includes a continuous sidewall having opposed first and second ends. The first end is closed by a first end cap. The second end is closed by a second end cap. The first end cap is integral with, being inseparable from, the first end of the continuous sidewall. The second end cap is connected sealably and removably to the continuous sidewall. The continuous sidewall is triangular, having three sides and three corners, between the first end and the second end, two of the three sides being straight and equal in length, one of the three sides being rounded, and each of the three corners being rounded. The gas detection and monitoring unit includes a gas sensor in sealed fluid communication with an ambient atmosphere outside the case, a temperature and humidity sensor in sealed fluid communication with the ambient atmosphere outside the case, a pressure sensor in sealed fluid communication with the ambient atmosphere outside the case, a data processor operatively connected to the gas sensor, the temperature and humidity sensor, and the pressure sensor, data storage and an information display operatively connected to the data processor, a calibration unit operatively connected to the data processor for calibrating the data processor to a predetermined gas concentration measured by the gas sensor, an externally operable switch for selectively connecting the data processor to the data storage to allow transfer of data from the data storage to the data processor, and a communication device operatively connected to at least one of the data processor and the data storage for enabling data transfer between an external destination and at least one of the data processor and the data storage. A power supply mounted in the case is operatively connected to power the gas detecting and monitoring unit. The gas sensor is mounted to the second end cap and is in sealed fluid communication via a first passage of the second end cap. The temperature and humidity sensor is mounted to the second end cap and is in sealed fluid communication via a second passage of the second end cap. The pressure sensor is mounted to the second end cap and is in sealed fluid communication via a third passage of the second end cap. The first passage, the second passage, and the third passage are separate from each other. The information display confronts the rounded one of the three sides of the continuous sidewall. The rounded one of the three sides of the continuous sidewall is transparent to enable the viewing of the information display therethrough. There is a catch formed in the first end of the case from which the apparatus can be suspended. A color-changing desiccant, a moisture indicator, within the case is for showing, by color changes, moisture in the case. The communication device is a wireless communication device for enabling wireless data transfer between the external destination and at least one of the data processor and the data storage. The gas detecting and monitoring unit further includes an inertial sensor sealed from the ambient atmosphere, and the data processor is operatively connected to the inertial sensor. The data process is for calculating at least one of, and preferably both, moisture uptake level and moisture uptake rate of the gas sensor, when the temperature and humidity sensor is sensing moisture of the ambient atmosphere outside the case.

BRIEF DESCRIPTION OF THE DRAWINGS

Referring to the drawings:

FIG. 5 is a top plan view of the embodiment of FIG. 1;

FIG. 6 is a bottom plan view of the embodiment of FIG. 1;

FIG. 7 is a bottom perspective view of the second end cap of the embodiment of FIG. 1;

FIG. 8 is a top perspective view of the embodiment of FIG. 7, illustrating set screws and attachment screws as they would appear withdrawn from the second end cap for illustrative purposes;

FIG. 9 is a section view taken along line 9-9 of FIG. 5; and

FIG. 10 is a section view taken along line 10-10 of FIG. 5.

DETAILED DESCRIPTION

Figure 1:
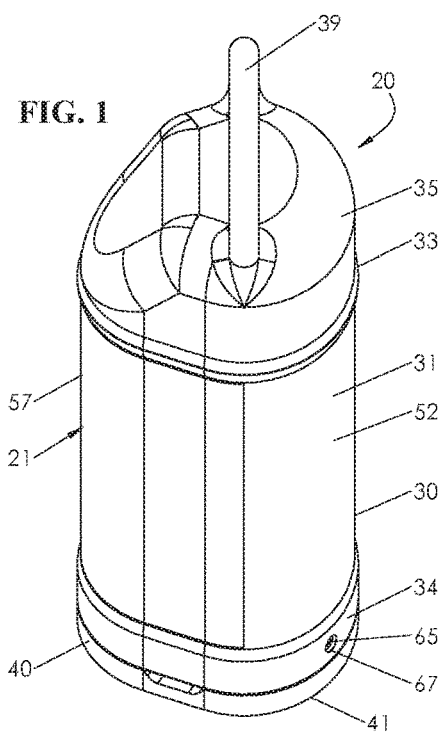
FIG. 1 is a top perspective view of a portable gas detecting and monitoring apparatus constructed and arranged in accordance with the principle of the invention, the apparatus includes a case having a first end closed by a first end cap formed with a catch from which the apparatus can be supported in a chosen environment, and a second end closed by a second end cap connected sealably and removably to the case.
Figure 2:
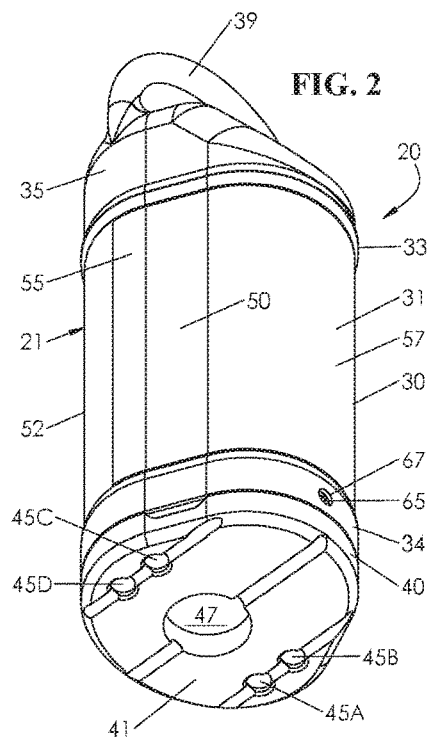
FIG. 2 is a bottom perspective view of the embodiment of FIG. 1.
Figure 3:
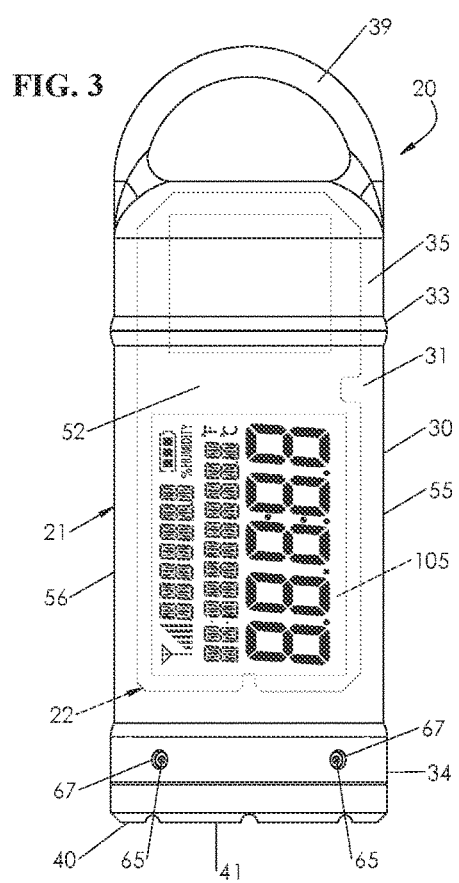
FIG. 3 is a front elevation view of the embodiment of FIG. 1.
Figure 4:
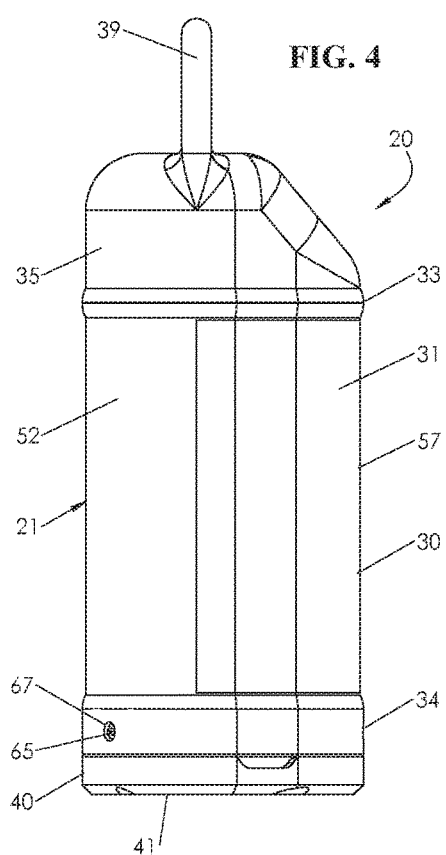
FIG. 4 is a right side elevation view of the embodiment of FIG. 1, the opposite left side elevation view being substantially the same thereof.

Turning now to the drawings, in which like reference characters indicate corresponding elements throughout the several views, attention is directed to FIGS. 1-5, 9, and 10 illustrating a portable gas detecting and monitoring apparatus 20 including case 21, and gas detection and monitoring unit 22 mounted in case 21 in FIGS. 3, 9, and 10. Case 21 includes continuous sidewall 30 having outer surface 31 and inner surface 32, and opposed ends 33 and 34. End 33 is a first or upper end of case 21. End 34 is a second or lower end of case 21. Upper end 33 is closed by end cap 35. End cap 35, an upper end cap of case 21, is integral with upper end 33, being inseparable from upper end 33 of continuous sidewall 30 of case 21. End cap 35 cooperates with inner surface 32 of continuous sidewall 30 to form volume 37 in FIGS. 9 and 10 within which unit 22 is positioned. Lower end 34 encircles opening 38 to volume 37. Volume 37 is for receiving unit 22 placed therein through opening 38. Continuous sidewall 30 and upper end cap 33 are integrally molded from a transparent plastic to enable the contents of volume 37 to be viewed therethrough for unit 22 inspection and for visually identifying therein moisture and other unwanted contaminants. End cap 35 is formed with a catch 39, a handle in the form of a half ring in this example, from which the apparatus can be supported/suspended in a chosen environment. Lower end 34 is closed by end cap 40. End cap 40, a lower end cap of case 21, is connected sealably and removably to continuous sidewall 30 for sealing and enclosing unit 22 in volume 37.

Continuous sidewall 30 is triangular, being a trilateral body, having three sides 50, 51, and 52, and three corners 55, 56, and 57, between upper end 33 and lower end 34. Preferably, sides 50, 51, and 52 and corners 55, 56, and 57 extend from upper end 33 to lower end 34. Sides 50 and 51 are straight and equal in length, side 52 is rounded (i.e. outwardly rounded), and each of the three corners is rounded (i.e. outwardly rounded), all of which defines the triangular shape of continuous sidewall 30, the trilateral body. Side 52 is a half ring or half pipe, in this example. The described shape of continuous sidewall 30, the trilateral body, is exceptionally strong, and extends to end cap 35. References FIGS. 5, 7, and 8 in relevant part, end cap 40 is a unitary body, of plastic in this example, including outer end 41, inner end 42, central recess 43 (FIG. 8), threaded holes 44 outboard of central recess 43 adjacent to the outer perimeter of end cap 40, and passages 45 outboard of central recess 43 adjacent to the outer perimeter of end cap 40. Passages 45 extend through cap 40 from outer end 41 to inner end 42. A coaxial hole or passage 47 (FIG. 9) extends from central recess 43 to outer end 41. The various passages are separate from one another, and do not interact with one another when apparatus 20 is assembled.

Referring to FIGS. 9 and 10, end cap 40 is inserted inner end 42 first into opening 38 of lower end 34 and sealably encloses opening 38 to volume 37 for sealably enclosing volume 37 that accommodates unit 22 thereby sealing enclosing unit 22 in volume 37. Threaded holes 44 accept screws 60 that secure end cap 40 to unit 22. An O-ring 61, a gasket, provided in a groove in end cap 40 seals inner surface 32 of continuous sidewall 30, preventing gas and moisture ingress into volume 37. End cap 40 is secured in place with set screws 65 in FIGS. 1-4, which thread into corresponding threaded holes 66 (FIGS. 8 and 9) in the side of end cap 40 through corresponding through holes 67 (FIGS. 1-4 and 9) through continuous sidewall 30 near lower end 34, sealing unit 22 in volume 37.

Unit 22 sealed in volume 37 of case 21 includes a variety of sensors, including gas sensor 70, temperature and humidity sensor 71, and pressure sensor 72. Gas sensor 70 is sealed in recess 43 in end cap 40 in sealed fluid communication with an ambient atmosphere outside case 21 via passage 47. Gas permeable membrane 80, a filter, used to prevent the ingress of moisture into recess 43 while at the same time enabling gas ingress to gas sensor 70 in recess 43, is sealed in place by O-ring 81, a gasket, that prevents gas and moisture ingress into volume 37. Gas sensor 70 is sealed into recess 43 by two O-rings 82, gaskets, one at each end of gas sensor 70, preventing gas and moisture ingress into volume 37.

Temperature and humidity sensor 71 is sealed a counterbore of one passage 45A at inner end 42 of end cap 40 in sealed fluid communication with an ambient atmosphere outside case 21 via passage 45A. Gas impermeable membrane 84, a filter that is permeable to humidity and impermeable to gas, is sealed in place by O-ring 85. O-ring 85 prevents gas and moisture ingress into volume 37.

Pressure sensor 72 is sealed a counterbore of another passage 45B at inner end 42 of end cap 40 in sealed fluid communication with an ambient atmosphere outside case 21 via passage 45B. Gas permeable membrane 87, a filter, is sealed in place by O-ring 88. O-ring 88 prevents gas and moisture ingress into volume 37. An identical pressure sensor, O-ring, and membrane are provided with passage 45C. Passage 45D is an audio/antenna port.

Unit 22 incorporates a printed circuit board ("PCB") assembly, including PCB 90 and sensor PCB 95, which carries, and electrically connects, the various components of unit 22. PCB 90 carries, and is electrically connected, to touch switch 100, externally operable reed switch 102 that acts as a secondary control, two additional externally operable reed switches, that act as additional controls, underneath an information display 105, a liquid crystal display ("LCD") in this example, that confronts, and that is visible through, side 52 of continuous sidewall 30, communication device 107 and universal communication socket 108, data processor 110, inertial sensor 111, data storage device 112, and calibration unit 113. Battery holder 115 connected to the back side of PCB 101 holds a battery 116, a dry cell battery pack in this example, that powers unit 22. When battery 116 is depleted, it may be removed from battery holder 115 and replaced with a fresh battery. Mounts 120 connect an end sensor PCB 95 to an end of PCB 90. Sensor PCB 95 is horizontal, and PCB 90 extends vertically upright from one end of sensor PCB 95. Gas sensor 70, temperature and humidity sensor 71, and pressure sensor 72 are carried by, and electrically connected to, sensor PCB 95, which is electrically connected to PCB 90. PCB 90 and sensor PCB 95 operatively connect data processor 110 to gas sensor 70, temperature and humidity sensor 71, pressure sensor 72, inertial sensor 111, data storage device 112, display 105, and calibration unit 113, all of which work in concert with one another.

Calibration unit 113 is operatively connected to data processor 110 for calibrating data processor 110 to a predetermined gas concentration measured by gas sensor 70, and for zeroing gas concentration levels in relation to humidity levels sensed by temperature and humidity sensor 71 for preventing gas sensor 70 leakage. Touch switch 100 is externally operable for selectively connecting data processor 110 to data storage device 112 to allow transfer of data from data storage device 112 to data processor 110. Communication device 107 is operatively connected to at least one of data processor 110 and data storage device 112, and preferably both, for enabling data transfer between an external destination and at least one of data processor 110 and data storage device 112. Communication device 107 is a conventional wireless communication device for enabling wireless data transfer between the external destination and at least one of data processor 110 and data storage 112. Communication device 107 employs one or more wireless communication protocols, such as radio frequency, Wi-Fi, and/or one or more other chosen wireless communication protocols. Inertial sensor 111 is sealed in volume 37 from the ambient atmosphere. A color-changing desiccant 130, a moisture indicator, in volume 37 of case 21, is for showing, by color changes, moisture in volume 37 of case 21. Apparatus 20 can be repaired or serviced, when desiccant changes color, such as from white to blue, indicating moisture in volume 37, simply by detaching lower end cap 45 from continuous sidewall 30 and withdrawing lower end cap 45 and unit 22 from volume 22 to enable the skilled worker to carry out necessary repairs and/or maintenance. In this example, desiccant 130 is carried by PCB 90, and is visible through side 52.

Unit 22 is assembled by connecting PCB 90 and sensor PCB 95, each equipped with the corresponding unit 22 components, with mounts 120 and connecting inner end 42 of end cap 40 to sensor PCB 95 via screws 60, advancing unit 22 into volume 37 through opening 38 and releasably connecting end cap 40 to continuous sidewall with set screws 65 for sealably and releasably/removably connecting end cap 40 to continuous sidewall 30, closing and sealing opening 38 and volume 37 sealably enclosing unit 22 in volume 37 of case 21. When volume 37 is sealed by end cap 40, apparatus 20 can float when dropped into a body of water. Sensor PCB 95 in volume 37 is connected to inner end 42 of end cap 40, and PCB 90 extends upright from sensor PCB 95 to exteriorly operable touch switch 100 at the top of end cap 35 where touch switch 100 is operated exteriorly. Inner end 42 of cap is shaped to correspond to the triangular shape of opening 38 of lower end 34 of case 21. Unit 22 in volume 27 is sufficiently spaced apart from the inner surfaces of case 21 for preventing unwanted contact between unit 22 and the inner surfaces of case 21.

Apparatus 20 is portable, in that it is easily taken up by hand and carried about for installation in a selected environment. Apparatus 20 is installed in an environment in which a particular gas is to be detected and monitored by securing apparatus 20 to selected location by suspending or supporting apparatus 20 in the chosen environment from catch 39. Apparatus 20 is switched on exteriorly, and operated exteriorly by, touch switch 100 and operates according to instructions preprogrammed into data processor 110, and operates with the ambient environment without the use of external controls. Touch switch 100 is conventional, is enclosed in volume 37 adjacent to end cap 35 opposite to catch 39, and is operated exteriorly by touching the outer surface of end cap 35 opposite to touch switch 100, requiring no physical contact with touch switch 100. The other switches of unit 22 are similarly exteriorly operable. Gas sensor 70, temperature and humidity sensor 71, and pressure sensor 72 in contact with the ambient environment concurrently detect and monitor, in real time, gas, temperature and humidity uptake, and pressure, specifically differential pressure, respectively, of the ambient environment. Real time monitoring of humidity level via temperature and humidity sensor 71 prevents gas sensor 70 leakage when data processor 100 calculates humidity uptake of gas sensor 70. Inertial sensor 111, in turn, and concurrently with the other sensors, senses, in real time, accelerations and moments that can occur if apparatus 20 is moved. Data processor 110 operatively coupled to the various sensors records and stores the data from the various sensors in data storage device 112, and displays the data on display 105 viewable through side 52. Display 105 is large, enabling it to display all of the sensor data and calculations made by data processor 110. Communication device 107 operatively connected to at least one of data processor 110 and data storage device 112, and preferably both, enables transfer of the data between an external destination and at least one of data processor 110 and data storage device 112. Communication device 107 is a conventional wireless communication device in a preferred embodiment for enabling wireless data transfer between the external destination and at least one of data processor 110 and data storage 112. If desired, a plug to an external device can be inserted into passage 45D for direct data transfer. Furthermore, an antenna can be plugged into passage 45D for increasing the wireless transmission distance of communication device 107. An audio device may also be plugged into passage 45D, as may be desired by the skilled worker. Calibration unit 113 operatively connected to data processor 110 and gas sensor 70 calibrates gas sensor 70 to a prearranged level to be measured from gas sensor 70. Unit 22 can incorporate an alarm, such as an audible and/or visual alarm, operatively connected to data processor 110 and set to issue an audible and/or visual alarm when a concentration of gas being measured by gas sensor 70 reaches a predetermined level, when unit 22 is calibrated, and when unit 22 is set to predetermined settings. In a particular embodiment, data processor 110 transmits a signal wirelessly to an external destination when a concentration of gas being measured by gas sensor 70 reaches a predetermined level to alert a skilled worker that the concentration of gas being measured has reached a predetermined level.

As described above, gas sensor 70, temperature and humidity sensor 71, and pressure sensor 72 in contact with the ambient environment concurrently detect and monitor, in real time, gas, temperature, humidity, and pressure, specifically differential pressure, respectively, of the ambient environment. During operation of unit 22, data processor 110 calculates the moisture, i.e. humidity, uptake level and moisture uptake rate of the gas sensor 70, and displays the calculated moisture uptake level and rate on display 105 in response enabling the skilled worker to extrapolate how long to deploy apparatus 20 at the chosen environment, when temperature and humidity sensor 71 is sensing moisture, i.e., humidity/moisture uptake level and humidity/moisture uptake rate, of the ambient atmosphere outside case 21. Furthermore, the calculated uptake level of gas sensor 70 enables the skilled worker to extrapolate the length of time needed to dry out the gas sensor 70 in a chosen controlled environment before apparatus 20 can be re-deployed. Unit 22 can incorporate an alarm, such as an audible and/or visual alarm, operatively connected to data processor 110 and set to issue an audible and/or visual alarm when the moisture uptake level measured by temperature and humidity sensor 71 reaches a predetermined level, and/or when the moisture uptake rate measured by temperature and humidity sensor 71 reaches a predetermined rate, to enable the skilled worker to remove apparatus 20 from the chosen environment for drying out and for preventing gas sensor 70 from filling up and leaking in real time. In a particular embodiment, data processor 110 transmits a signal wirelessly to an external destination when the moisture uptake level measured by temperature and humidity sensor 71 reaches a predetermined level, and/or when the moisture uptake rate measured by temperature and humidity sensor 71 reaches a predetermined rate, to enable the skilled worker to remove apparatus 20 from the chosen environment for drying out gas sensor 70 and for preventing the gas sensor 70 from filling up and leaking in real time.

The present invention is described above with reference to illustrative embodiments. However, those skilled in the art will recognize that changes and modifications may be made in the described embodiments without departing from the nature and scope of the present invention. Various further changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, Having fully described the invention in such clear and concise terms as to enable those skilled in the art to understand and practice the same, the invention claimed is:

1. A portable gas detecting and monitoring apparatus, comprising:
   a case, the case includes a continuous sidewall having opposed first and second ends, the first end is closed by a first end cap, the second end is closed by a second end cap, the second end cap is connected sealably and removably to the continuous sidewall, the continuous sidewall is triangular being a trilateral body having three sides and three corners, between the first end and the second end, two of the three sides being straight and equal in length, one of the three sides being rounded, and each of the three corners being rounded;
   a gas detection and monitoring unit enclosed and sealed in the case from an ambient atmosphere outside the case, the gas detection and monitoring unit includes:
      a gas sensor in sealed fluid communication with the ambient atmosphere outside the case;
      a temperature and humidity sensor in sealed fluid communication with the ambient atmosphere outside the case;
      a pressure sensor in sealed fluid communication with the ambient atmosphere outside the case;
      a data processor operatively connected to the gas sensor, the temperature and humidity sensor, and the pressure sensor;
      data storage and an information display operatively connected to the data processor;
      a calibration unit operatively connected to the data processor for calibrating the data processor to a predetermined gas concentration measured by the gas sensor;
      an externally operable switch for selectively connecting the data processor to the data storage to allow transfer of data from the data storage to the data processor; and
      a communication device operatively connected to at least one of the data processor and the data storage for enabling data transfer between an external destination and at least one of the data processor and the data storage; and
   a power supply mounted in the case, the power supply being operatively connected to power the gas detecting and monitoring unit.

2. The portable gas detecting and monitoring apparatus according to claim 1, wherein the gas sensor is mounted to the second end cap and is in sealed fluid communication via a first passage of the second end cap.

3. The portable gas detecting and monitoring apparatus according to claim 2, wherein the temperature and humidity sensor is mounted to the second end cap and is in sealed fluid communication via a second passage of the second end cap.

4. The portable gas detecting and monitoring apparatus according to claim 3, wherein the pressure sensor is mounted to the second end cap and is in sealed fluid communication via a third passage of the second end cap.

5. The portable gas detecting and monitoring apparatus according to claim 4, wherein the first passage, the second passage, and the third passage are separate from each other.

6. The portable gas detecting and monitoring apparatus according to claim 1, wherein the information display confronts the rounded one of the three sides of the continuous sidewall, and the rounded one of the three sides of the continuous sidewall is transparent to enable the viewing of the information display therethrough.

7. The portable gas detecting and monitoring apparatus according to claim 1, further comprising a catch formed in the first end of the case from which the apparatus can be suspended.

8. The portable gas detecting and monitoring apparatus according to claim 1, further comprising a color-changing desiccant within the case.

9. The portable gas detecting and monitoring apparatus according to claim 1, wherein the communication device is a wireless communication device for enabling wireless data transfer between the external destination and at least one of the data processor and the data storage.

10. The portable gas detecting and monitoring apparatus according to claim 1, wherein the gas detecting and monitoring unit further includes an inertial sensor sealed from the ambient atmosphere for sensing in real time accelerations and moments if the apparatus is moved, and the data processor is operatively connected to the inertial sensor.

11. The portable gas detecting and monitoring apparatus according to claim 1, wherein the first end cap is integral with, being inseparable from, the first end of the continuous sidewall.

12. The portable gas detecting and monitoring apparatus according to claim 1, wherein the data processor calculates in real time at least one of moisture uptake level and moisture uptake rate of the gas sensor, when the temperature and humidity sensor is sensing moisture of the ambient atmosphere outside the case.

* * * * *